United States Patent [19]

Kallos

[11] 4,042,326
[45] Aug. 16, 1977

[54] METHOD OF QUANTITATIVELY DETECTING CHLOROMETHYL METHYL ETHER AND/OR BIS-CHLOROMETHYL ETHER WITH IMPROVED SENSITIVITY

[75] Inventor: George J. Kallos, Saginaw, Mich.

[73] Assignee: The Dow Chemical Company, Midland, Mich.

[21] Appl. No.: 611,939

[22] Filed: Sept. 10, 1975

Related U.S. Application Data

[63] Continuation-in-part of Ser. No. 536,709, Dec. 26, 1974, abandoned.

[51] Int. Cl.$^2$ .......................................... G01N 31/08
[52] U.S. Cl. .............................. 23/230 R; 23/230 M; 23/232 C; 23/253 R; 23/254 E; 23/255 E; 73/23.1; 73/61.1 C; 260/613 D; 260/615 R
[58] Field of Search ............ 23/232 R, 232 C, 253 R, 23/254 E, 254 R, 255 R, 255 E, 230 R, 230 M; 73/23.1, 61.16; 260/613 D, 615 R

[56] References Cited

U.S. PATENT DOCUMENTS

| | | | |
|---|---|---|---|
| 3,807,217 | 4/1974 | Wilkens et al. | 23/232 C |
| 3,934,981 | 1/1976 | Ault et al. | 23/254 R X |

OTHER PUBLICATIONS

Shadoff et al., "Determination of Bis(chloromethyl)Ether in Air by Gas Chromatography–Mass Spectrometry," Anal. Chem. vol. 45, No. 14, Dec. 1973, pp. 2341–2344.

Ton et al., "Kinetic Study of the Stabilities of Chloromethyl Methyl Ether and Bis(chloromethyl)Ether in Humid Air," Anal. Chem. vol. 46, No. 12, Oct. 1974, pp. 1866–1869.

Primary Examiner—Norman Yudkoff
Assistant Examiner—Barry I. Hollander
Attorney, Agent, or Firm—Glenn H. Korfhage; Arthur J. Young

[57] ABSTRACT

Method of quantitatively determining chloromethyl methyl ether and/or bis-chloromethyl ether at greater sensitivity comprising utilizing an alkali metal salt of a lower alcohol and a readily detectable organic hydroxy compound in lower alcohol medium in a salt-to-hydroxy compound molar ratio of from about 0.2:1 to about 5:1 to react, when warmed, with either or both of said ethers, to form derivatives thereof; adding water to the reaction mixture and an immiscible hydrocarbon solvent; agitating and partitioning the mixture and directing at least a portion of the immiscible organic solvent extract onto a suitable gas chromatograph, preferably packed with glass beads with a stationary liquid phase thereon and more preferably with the beads coated with OV275 as the liquid phase; and eluting the reaction product or products off the column and through a detector therefor with an inert gas.

26 Claims, 2 Drawing Figures

METHOD OF QUANTITATIVELY DETECTING CHLOROMETHYL METHYL ETHER AND/OR BIS-CHLOROMETHYL ETHER WITH IMPROVED SENSITIVITY

CROSS REFERENCE TO RELATED APPLICATIONS

This application is a continuation-in-part of Ser. No. 536,709 filed Dec. 26, 1974, now abandoned.

This application discloses and claims a method which is an improvement over the method of copending application Ser. No. 378,480, filed July 12, 1973, in which is disclosed, generally, the preparation of a derivative of either or both of the ethers by reaction with, in lower alcohol medium, the alkali metal salt of a lower alcohol, or of an aromatic hydroxy compound disclosed herein, adding water and an immiscible hydrocarbon solvent to the reaction mixture, agitating and then separating the phases and directing at least a portion of the solvent phase onto a gas chromatograph and eluting the derivative from the column and through a detector therefor.

BACKGROUND OF THE INVENTION

1. Field of the Invention

The invention relates to an improved method of quantitatively determining either or both of chloromethyl methyl ether and bis-chloromethyl ether present in a fluid sample, i.e., in a gas such as air or the atmosphere above an organic reaction medium, or in a liquid such as an organic reaction medium or stream, such as the reaction mixture occurring in the manufacture of ion exchange resin. The invention more particularly relates to an improved method of determining chloromethyl methyl ether or bis-chloromethyl ether at a concentration as low as 0.1 part per billion (ppb).

2. The Prior Art

In fairly recent times industrial health and safety work has come to encompass studies of the effects on human subjects of being exposed to even very low levels of chemical substances dispersed in the plant environment in which production workers carry on their duties. Very recently concern was raised about the possible adverse effects of exposure to chloromethyl methyl ether, a reactant used in the manufacture of ion exchange resins, and to bis-chloromethyl ether, a compound formed under certain conditions in the manufacture of chloromethyl methyl ether. Chloromethyl methyl ether (CMME) is at least irritational to the eyes and bis-chloromethyl ether (bis-CME) is apparently a carcinogen. It is of interest to determine the concentration of the bis compound in a product stream as this concentration usually has a direct bearing on the amount which escapes into the atmosphere in the vicinity of a chemical manufacturing process in which the bis compound occurs. It is also of extreme interest and importance to determine the concentration level of both of these compounds in a plant environment so that meaningful toxicology studies may be carried out for that level of exposure. It is of vital importance that such detection methods are available for the protection of industrial workers.

In early studies of the occurrence of chloromethyl methyl ether and bis-chloromethyl ether resort was had to use of a gas chromatograph in combination with a mass spectrometer, but studies showed that the high level of toxicity of these compounds necessitated their detection at concentration levels somewhat below the capabilities of this instrument combination.

In more recent work, the subject of the said copending patent application, it was discovered that greatly improved sensitivity was obtained upon (1) bringing a fluid sample containing either or both of these ethers into admixture with an alkali metal salt of an organic hydroxy compound such as a lower alcohol or an aromatic hydroxy compound such as a phenol, and preferably a chlorophenol, in lower alcohol medium, whereupon an even more complex ether is formed, by way of a derivative, (2) adding water and immiscible organic solvent to the reaction mixture and taking up the derivative into the solvent phase, (3) directing at least a portion of the solvent phase onto a gas chromatograph, and (4) eluting with an inert gas such as nitrogen, whereby such derivative is readily separated on the column with great specificity and sensitivity and is readily detected, as by a flame ionization detector, and more preferably by an electron capture detector when the derivative is of a halogenated organic hydroxy compound with one of the ethers.

SUMMARY OF THE INVENTION

The method of the invention is based on the discovery that upon providing an alkali metal salt of a lower alcohol in admixture with a readily detectable organic hydroxy compound selected from a haloalkanol, a halophenol, an alkoxy phenol, an alkoxy halophenol, an alkyl phenol, an alkyl halophenol, unsubstituted phenol, a thiophenol, a halothiophenol, a halogenated pyridinol and an unsubstituted pyridinol, in a molar ratio of from about 0.2:1 to 5:1, and in lower alcohol medium, and on introducing thereinto a sample of fluid containing either or both of chloromethyl methyl ether or bis-chloromethyl ether, a highly detectable derivative of such ethers present is formed, said derivative containing at least one moiety derived from said organic hydroxy compound. An aqueous medium, such as water or an aqueous solution of a salt former, and an immiscible organic solvent are added to the reaction mixture, agitated, and separated, and on directing at least a portion of the solvent phase through a suitable gas chromatograph and eluting the reaction mixture therefrom with an inert gas and into a detector for the derivatives, the same are quantitatively detected with great sensitivity and specificity, permitting quantitative determination of said chloromethyl ethers present in a gas such as air at a concentration level as low as 0.1/ppb, in most instances, i.e., in the absence of interfering substances, which interfering substances are very seldom encountered. Preferably the ratio of said salt to said readily detectable organic hydroxy compound is about 1:1. It is also preferred that the chromatographic column be packed with glass beads having a stationary liquid phase thereon and even more preferred that the glass beads be lightly coated with the commercial preparation OV275 as the liquid phase. When the molar ratio of said salt to said readily detectable organic hydroxy compound is less than about 1:1 it is highly desirable, though not strictly essential, that sufficient salt former be added to said water, or equivalently, that a solution of said salt former be used in the place of the said water, to assure retention of any of said hydroxy compounds present in the aqueous phase during partitioning with the immiscible organic solvent.

THE DRAWINGS

The invention, as well as additional objects and advantages thereof, will be best understood when the following detailed description is read in connection with the accompanying drawings in which FIG. 1 is a partly diagrammatic and partly schematic representation of apparatus for use in analyzing fluid samples in accordance with this invention in which the samples are gas samples, and in which

DETAILED DESCRIPTION OF THE DRAWING

Figure 1:
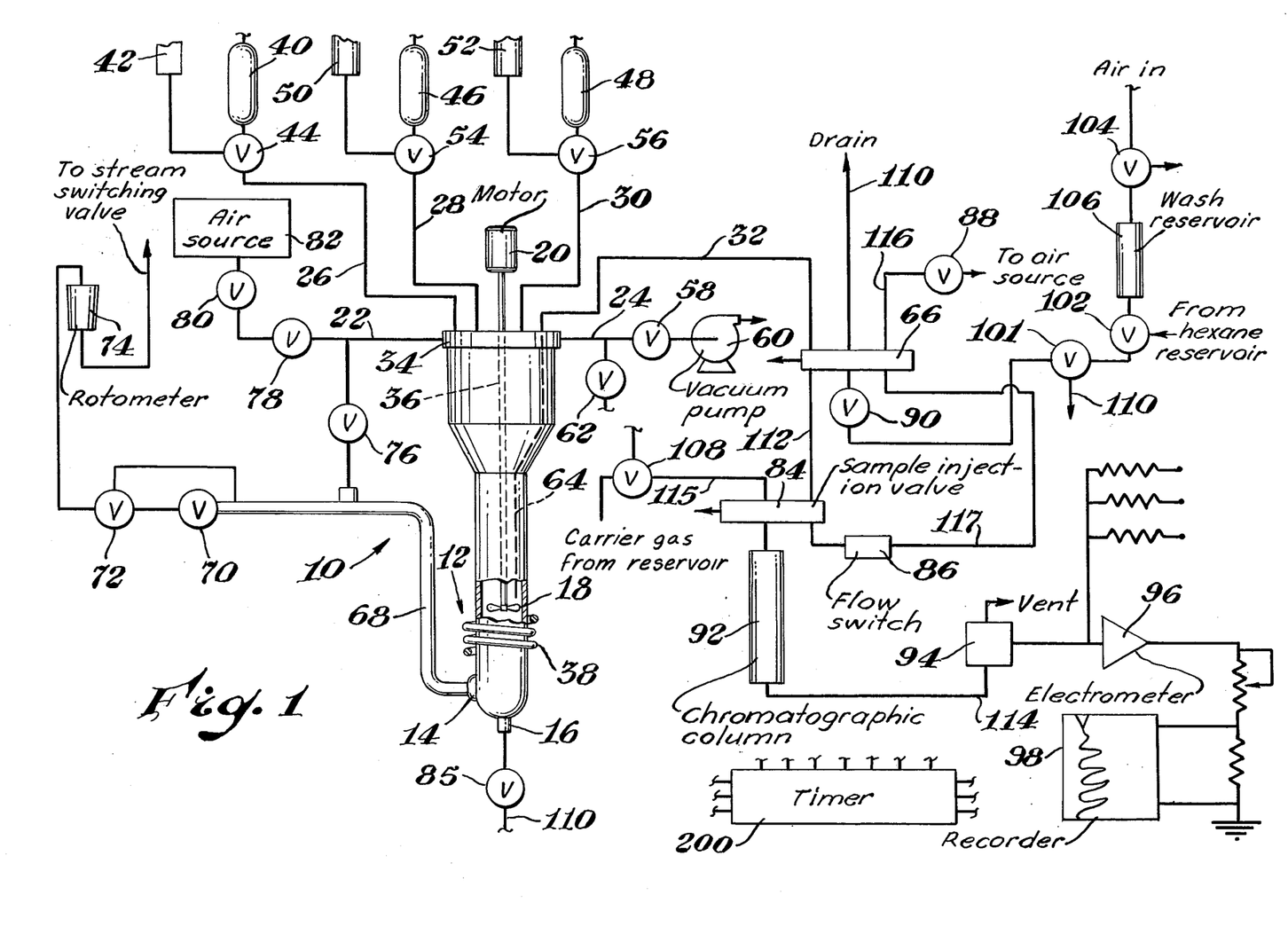

Referring to FIG. 1 of the drawing, there is shown apparatus for analyzing gas samples, indicated by the numeral 10, including a scrubber 12 having an inlet 14 and an outlet 16 near and at the bottom thereof, respectively. The scrubber 12 has a stirrer 18 therein which is actuated by an externally located motor 20. Six lines or conduits 22, 24, 26, 28, 30, 32 extend through the closed top 34 of the scrubber, as does the shaft 36.

A heat tape 38 surrounds part of the lower part of the scrubber 12.

The line 26 is coupled to a measuring pipet 40 and a constant level tank 42 through a three way valve 44. The lines 28 and 30 are similarly coupled to pipets 46 and 48, respectively, and to tanks 50 and 52, respectively, through the three way valves 54 and 56, respectively.

The line 24 is coupled through a valve 58 to a vacuum pump 60. The line 24 may also be opened to the atmosphere through the valve 62.

The line 32 is coupled to the dip pipe 64 and to a six port chromatograph valve 66.

A line 68 is coupled to the scrubber inlet 14 and extends through valve 70, flow control valve 72 and rotometer 74 to an air source (via a stream switching valve, for example). The line 68 is also coupled to the line 22 through valve 76. The line 22 is also coupled through needle valve 78 and valve 80 to a source 82 of pressurized air.

The outlet 16 of the scrubber 12 opens through the valve 85 to drain 110.

Carrier gas such as oil-free nitrogen, from a reservoir (not shown) is coupled through valve 108 and line 115 to the sample injection valve 84 and thence through the chromatographic column 92 to direct the gas therethrough for eluting sample components off the column and through the detector 94.

The line 112 connects the line 32 through the chromatograph valve 66 to the sample injection valve 84.

The gaseous output of the chromatographic column 92 is conveyed through the line 114 to an electron capture or other suitable detector 94 whose electrical output is coupled to an electrometer 96 or other suitable amplifier and thence to a recorder 98 or other readout device.

A suitable solvent such as hexane, for example, from a reservoir (not shown) is applied to a wash reservoir 106 through three way valve 102. The upper end of the reservoir 106 is coupled to a three way valve 104 which is also coupled to an air source (which may be the same or like the source 82).

The other side of the valve 102 is coupled through valve 101 and valve 90 to the multiport chromatographic valve 66. Valve 101 may also be coupled to a drain which may be the same or like drain 110.

The sample injection valve 84 is coupled through the line 117 and flow switch 86 to the chromatographic valve 66.

A line 116 is coupled through valve 88 between an air source (not shown) and the multiport chromatographic valve 66.

OPERATION OF FIG. 1 APPARATUS

At the start of the analytical cycle the scrubber 12 is empty. The valve 54 is actuated to drain a reagent, i.e. a reagent which will react with chloromethyl methyl ether (CMME) or bis-chloromethylether (bis-CME) to form a derivative, from the pipet 46 into the scrubber 12 and is then closed. The pipet 46 has been filled from the constant level tank 50. At this time the valve 58 is opened to allow vacuum to be pulled on the scrubber 12. Sample air is then pulled through the rotameter 74 and the flow controller 72 through the reagent in the bottom of the scrubber to the top of the scrubber and out the tubing line 24. After a preset length of time (usually about 5 to 15 minutes), the valve 62 is opened to partially or fully relieve the vacuum which will reduce air flow through the scrubber 12. Heat is applied to the reagent in the scrubber by an external heat tape 38 wrapped around the bottom of the scrubber 12.

Sample volume is dependent upon concentration of CMME and bis CME in the air sample. For 10 ppb or less concentration a sample size of 10 to 40 liters can be used. For higher concentrations a correspondingly smaller sample should be taken.

The stirrer motor 20 is activated simultaneously with heating to provide agitation or a gas sparger, not shown, may be used for agitation. After the liquid in the scrubber 12 is brought to at least slightly above room temperature, e.g., about 25 to about 100° C. (on time basis by experience), the valve 44 is actuated to drain water into the scrubber 12 from the measuring pipet 40 which is filled from constant level tank 42.

After water has been admitted, the valve 56 is actuated to drain into the scrubber a solvent such as hexane from the measuring pipet 48 which has been filled from a constant level tank 52. At this time, the valve 58 is closed to stop the pulling of vacuum on the scrubber. The stirrer motor 20 continues to run to mix the reaction mixture in the scrubber adequately. The valve 80, which is connected to a pure filtered pressurized air source (clean compressed air from an air tank is suitable), is opened. The valve 78 is a needle valve that restricts and regulates air flow to low flow rates. After the admixture is mixed adequately in the scrubber 12, the stirrer motor 20 is stopped and the hexane and water-lower alcohol mixture are allowed to separate, with the hexane floating on top.

After a sufficient time, e.g., about 2 minutes, has elapsed for the solution to separate, the valve 62 is closed, as are valves 44, 54, and 56 if the latter three valves have not already been actuated to refill pipets 40, 46, 48. The stream switching valve (or equivalently, valves 70 and 72) is closed and valve 76 is opened to maintain equilibrium between the pressure in line 68 and that in the scrubber 12. The increasing air pressure within the scrubber 12 then forces substantially all the hexane layer up the dip pipe 64 which is adapted to terminate in the hexane layer just above the liquid-liquid interface. Since the pressure is equalized in line 68 and the scrubber 12, the level of the liquid-liquid interface is maintained constant just below the end of the dip pipe 64, while the major portion of the hexane is driven up the dip pipe.

From the dip pipe 64, the hexane solution is pushed by air pressure through the transfer line 32 through the six port chromatograph valve 66 and through a measuring bore of the sample injection valve 84 to flow switch 86.

As soon as hexane solution reaches the flow switch 86, the chromatograph valve 66 and valves 88 and 90 are actuated thereby. The valve 88 is connected to a pressurized, filtered source of air. The valve 90 is normally open to drain to allow air to escape while hexane solution is transferred. Actuation of the valves 66, 90 and 88 places the liquid filled line on both sides of sample valve 84 under pressure to prevent formation of air bubbles in the hexane. After air pressure is applied to the hexane, the valve 84 is actuated to inject a measured portion of the hexane as a sample into the chromatograph column 92 where a typical gas chromatograph separation is completed (Beckman Model 320 DF or Bendix Model 6000 may be used, for example). Components from the column 92 are eluted into a suitable detector 94 such as a flame ionization detector but more preferably is an electron capture detector, for example, which, when a halogenated compound is present, will cause a decrease of electrical current through the detector. The small decrease in current is sensed by an electrometer 96, amplified, and displayed on recorder 98.

A short time after a sample is injected onto the gas chromatograph, the valve 90 is opened and hexane that was trapped in the transfer tubing on either side of the injection valve 84, is forced by air pressure into drain 110 through the valve 101. After a short period of time, the valve 88 is shut and the valve 66 is actuated to its original position. The valve 90 is left open ready for the next transfer of liquid.

At this time, the valve 85 is opened to drain 110 to remove residual liquid from the scrubber 12. At this same time, valves 101 and 102 are actuated. After a small time delay, the valve 104 is also actuated. The valve 104 is connected to a source of clean pressurized air and to the top of the wash reservoir 106. The wash reservoir 106 has been filled previously through the valve 102 with hexane from the reservoir connecting to the valve 102. Pressurized air then forces the hexane from the wash reservoir 106 through valves 102, 101, 90, multiport valve 66, line 117, flow switch 86, valve 84, again through multiport valve 66 via transfer lines 112 and 32 to the scrubber 12 and out valve 85 to drain 110. This wash effectively removes any residual sample left in any valves or in the scrubber 12.

After the hexane has been completely drained through the system, valve 104 closes followed by closure of valves 101, 102 and 85. The wash reservoir 106 fills again from the reservoir connected through valve 102 to be ready for another wash cycle.

The pressure regulator 108 is part of the gas chromatograph unit and is used to control the flow of carrier gas.

The system is then ready for collection and analysis of another sample.

The various valves are remotely actuated valves. Apart from the valves actuated by the flow switch 86, e.g. valves 88 and 90, they and the motor 20 are actuated by means of a sequential timing device 200 of any of a number of types well-known to those skilled in the instrumentation art. The timer is shown symbolically and is not shown connected to valve activators to avoid presenting an overly complex drawing which would simply be confusing.

In practicing the embodiments described in Ser. No. 378,480 wherein, for example, a large excess of sodium methoxide is dissolved in methanol with a chlorinated phenol such as 2,4,6-trichlorophenol to form as a reactive species, the corresponding phenate, it was discovered that the respective derivatives being detected, believed formed according to the reactions were formed at only about a 5 percent yield based on the amount of bis-CME or CMME initially present.

The present improved method is based on the discovery that yields of the derivatives are acutely dependent on the ratios of the salt and the hydroxy compound. In particular, the large excess of sodium methoxide vis-a-vis the chlorophenol, i.e., the salt to hydroxy compound ratio, suggested by Ser. No. 378,480 actually suppresses formation of the derivatives as is illustrated by comparison Run 1 which follows in the table.

Where the total number of moles of said salt is at least equal to the sum of the moles of CMME plus two times the moles of bis-CME, and where the total number of moles of said hydroxy compound is at least equal to the sum of the moles of CMME and bis-CME, it has now been discovered that by utilizing said salt and said hydroxy compound in molar proportions of about 0.2:1 to 5:1 in the lower alcohol medium, the yields of derivatives are greatly increased, generally by a factor of at least about 4. Preferably, said salt-to-hydroxy compound ratio is about 1:1. For most practical applications, from about 0.03 to about 0.5 mole of each of the hydroxy compound and the salt are employed per liter of the lower alcohol, preferably about 0.1 mole of each per liter of lower alcohol.

Utilizing preferred concentrations of preferred reagents and an electron capture detector the method is capable of quantitatively determining bis-CME and CMME concentrations as low as about 0.1 ppb in a gas, e.g., air. This corresponds to 3.3 nanograms per liter (ng/l) and 4.7 ng/l of air, respectively for CMME and bis-CME, as calculated from the Ideal Gas Law.

The method is applicable to the quantitative detection of CMME and bis-CME in a gas such as air or in the gaseous atmosphere above a liquid reaction mixture e.g., a mixture of reactants and products in the manufacture of ion exchange resins, or, other mixtures where HCl and formaldehyde are present. Gas samples, as indicated above in describing the use of the apparatus of FIG. 1, are processed by drawing a sufficient quantity of the sample through a scrubber containing the metal salt and the hydroxy compound in the lower alcohol medium. Generally 10 to about 40 liters of gas is a practical limit for processing a gas with traces of CMME or bis-CME approaching the detection limits of this method. An appropriately smaller gas sample is used if the concentration of the material to be detected is higher than about 10 ppb.

The method is also applicable to the analysis of liquids containing CMME or bis-CME, e.g. a reaction mixture occurring in the manufacture of ion exchange resin containing methanol, methylal, and ethylene dichloride in addition to CMME. As is apparent, alcohols, unhalogenated ethers and halogenated hydrocarbons do not normally interfere with derivative formation nor do they interfere with the separation and detection process.

It is definitely preferred, as a practical matter, that readily detectable hydroxy compounds are not taken up in the organic solvent extraction step illustrated above by the use of hexane. If taken up in the organic solvent, the hydroxy compounds tend to complicate the subsequent separation and/or detection steps in one way or another, such as by generating additional spectral peaks. Of most concern, however, are the halogenated hydroxy compounds which, concentrated as they elute from the chromatographic column, provide such a strong input to the electron capture detector that the accuracy of the detector is adversely affected thereby. If that happens, the detector cannot be used again until it recovers from the strong impulse, usually after several hours or more.

To avoid transfer of the hydroxy compounds used herein during the extraction step, especially when the salt to hydroxy compound molar ratio is less than about 1:1, the water used to help "salt" the derivative into the solvent phase is replaced by a dilute solution of a salt former, i.e., a material such as alkali metal hydroxide, conveniently, sodium hydroxide, which will convert the hydroxy compound from weakly ionized to highly ionized form and keep it in the water-alcohol phase. If more convenient or otherwise desirable, aqueous solution of alkali metal salt of lower alcohol may be used instead of caustic solution. This, in effect, is what was done in situ in Ser. No. 378,480 where, for example, the sodium methoxide:chlorophenol ratio was high, except that there, the excess sodium methoxide was present before the derivatives were formed, whereas here the excess is not added until after the derivatives are formed. In any event, an aqueous solution of from about 1 to 5 normal in the salt former is generally used in sufficient volume, e.g., from about 50 to 150 percent, preferably 50 to 100 percent, of the volume of the lower alcohol medium, to assure extraction of the hydroxy compound, such as 2,4,6-trichlorophenol, does not occur.

As used herein, lower alcohol means alkanol containing 1 to 5 carbons and preferably 1 to 3 carbons.

Preferably the alkali metal salt of lower alcohol used is the salt of the lower alcohol medium used. Thus, a much preferred combination is sodium methoxide and methanol, although sodium ethoxide and ethanol are also quite satisfactory. The reactivity of the salts decreases with increasing chain length of the alkyl portion. The alkali metals referred to are preferably sodium, potassium, lithium or cesium.

The term readily detectable organic hydroxy compound as used herein refers to organic hydroxy compounds which form a derivative, with CMME or bis-CME, that is readily detected by a flame ionization detector or an electron capture detector. While this is a slight misnomer it is readily perceived and understood by those skilled in the art. Hydroxy compounds with a substantial carbon content such as six or more carbons preferably with hydrogen thereon are rather readily detected by the flame ionization detector, while the more sensitive electron capture detector is responsive to those compounds containing halogen, and preferably a plurality or more of halogen atoms per molecule. The most preferred halogenated compounds from the standpoints of availability, cost, and stability are the chloro and bromo compounds. The most preferred hydroxy compounds are the chloro or bromo phenols including the alkyl, alkoxy, and otherwise unsubstituted, phenols.

In carrying out the collection and detection process using the apparatus described above it is generally suitable to use about 10 to 15 milliliters of the lower alcohol medium as the scrubber or absorption liquid containing from about 0.03 to about 0.5 mole per liter of each of the salt and the hydroxy compound in the molar ratios of salt to hydroxy compound set forth above. After collection of the CMME and/or bis-CME from the preselected gas volume, the reaction mixture is warmed slightly to facilitate derivative formation. The temperature is not sharply critical. Generally warming the mixture briefly to about 25° to about 100° C. suffices, e.g., for 3 to 5 minutes. Then an amount of water or dilute salt former solution in volume equal to approximately 50 to 150 percent of the lower alcohol volume, preferably 50 to 100 percent, is added, in addition to a measured quantity of organic solvent. Suitable organic solvents, include such liquid hydrocarbons as, e.g., pentane, hexane, octane iso-octane, decane, benzene and alkyl benzene or a mixture thereof. Similar hydrocarbon solvents with similar viscosities are generally suitable.

The magnitude of the preselected volume of solvent employed is not sharply critical. The volume should be sufficiently large so that a liquid extraction step can be practically carried out, but unduly large volumes are not recommended because unnecessary dilution of the derivatives results. It has been found convenient to employ a volume in the range of about 5 to about 25 percent of the volume of the lower alcohol, preferably 10–20 percent. Similarly, the volume of aqueous medium is not particularly critical, the foregoing quantities being those found to be most practical in achieving good separation of the derivatives from the remaining components without undue dilution. The two-phase mixture is agitated sufficiently to intermingle the phases during 2 or 3 minutes and is then allowed to settle. Settling occurs promptly, usually within about a minute, whereupon the organic solvent phase is withdrawn and directed to the measuring portion of a sample injection valve for a gas chromatograph where selection of a sample size of about 2 microliters suffices.

The chromatograph may be, for example, a Pye Model 104 (Phillips Electronic Co.) gas chromatograph equipped with a Ni$^{63}$ electron capture detector, a series 1400 (Varian Assoc.) or a 5700 A (Hewlett-Packard Corp.) gas chromatograph similarly equipped, or any comparable chromatograph.

The chromatographs utilize a column packed with particulate silicate but more preferably glass beads about 100 to 120 mesh (U.S. Sieve Series) coated with a stationary liquid phase. An example of a suitable silicate is chromosorb WHP. The liquid phase may be OV-17, but is preferably OV-275, a highly polar cyano silicone polymer, manufactured by Ohio Valley Specialty Chemical Company, Marietta, Ohio, and marketed by Anspic Company, Inc., which facilitates better separation by the instant method without adversely affecting the stability of the derivatives. Preferably the columns are steel or glass columns about ⅛ inch by 6 to 15 feet long equipped for on column injection, i.e., with the injection taking place into a section of the column at about the same temperature as the rest of the column, and not into a preheater section held at a substantially higher temperature. A temperature of about 175° C in the injection zone and of about 140° C for the remainder of the column is satisfactory, although the temperature is not sharply critical. A suitable flow rate for the carrier gas used for elution is about 30 ml per minute.

The alkali metal salt of a lower alcohol as used herein may be purchased or made simply by dissolving an alkali metal in the desired alcohol. The organic hydroxy compounds may generally be purchased but purity should be ascertained or obtained to assure reproducible results.

Figure 2:
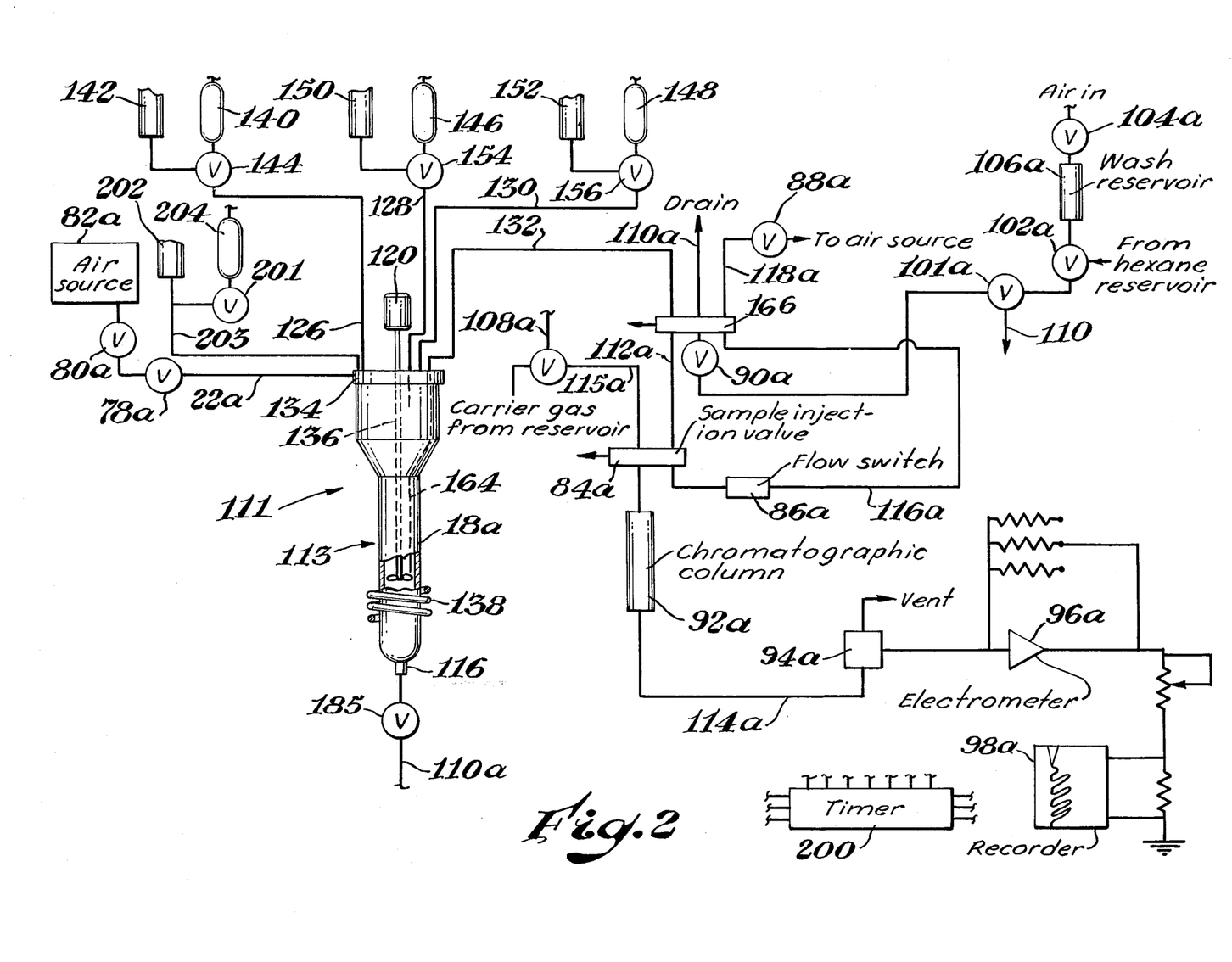
FIG. 2 is a partly diagrammatic and partly schematic representation of apparatus for analyzing liquid samples according to the invention.

The apparatus shown in FIG. 2 is suitable for the analysis of liquid samples and in operation is substantially identical to the apparatus of FIG. 1 except that the apparatus sections for bringing the gas sample in through the lower part of the scrubber or reaction section, and the vacuum pump and lines thereto have been eliminated and instead there is provided a measuring pipet 204, a three way valve 201, a reservoir 202 for filling pipet 204 (which reservoir 202 may represent, for example, means for sampling a liquid product stream suspected of containing bis-CME or CMME), and line 203 for delivering liquid sample into the reactor 113. If desired, any other convenient means may be used for introducing liquid sample into the reactor 113.

EXAMPLES

In each of a series of runs carried out to demonstrate the greatly improved sensitivity of the present method various methanol solutions each containing 2,4,6-trichlorophenol and sodium methoxide in various amounts and molar ratios were used in respective runs. In each run, 15 milliliters (ml) of methanol solution was placed in a small screw cap vial and 10 microliters (μl) of a standard solution of CMME and bis-CME added thereto. The 10 μl contained a total of 3.18 micrograms (μgm) of CMME and 1.33 μgm of bis-CME. The vials were capped and warmed on a steam bath for about 5 minutes and then cooled and 15 ml of 2N NaOH solution and 2 ml of hexane were added to each vial. The contents of each vial were shaken for about 5 minutes and then allowed to stand for at least a minute for the phases to separate before 2 μl of the hexane layer were taken up and injected into a gas chromatograph of the type described above. Net peak heights were observed and are tabulated in the table below along with the reagent concentration used. On comparing the response obtained in the comparison run with the responses obtained using the reagent proportions according to the present method it is seen that the sensitivity of the method has been improved by a factor in the range of about 3 to about 8.

TABLE

| | Concentration of Reagents | | | | Net Peak Height × 32 (mm) | |
|---|---|---|---|---|---|---|
| Run No. | 2,4,6-gms/l. | 2,4,6-trichlorophenol moles/l | NaOCH$_3$ moles/l | NaOCH$_3$:TCP Molar ratio | CMME | bis-CMe |
| Comparison 1 | 5 | 0.025 | 0.463 | 18.52:1 | 210 | 38 |
| 1 | 6.9 | .035 | .039 | 1.11:1 | 880 | 184 |
| 2 | 9.9 | .050 | .065 | 1.3:1 | 800 | 152 |
| 3 | 10 | .051 | .037 | .73:1 | 620 | 148 |
| 4 | 10 | .051 | .081 | 1.59:1 | 648 | 144 |
| 5 | 16 | .081 | .080 | .99:1 | 1440 | 216 |
| 6 | 16 | .081 | .143 | 1.77:1 | 1240 | 224 |
| 7 | 16 | .081 | .296 | 3.66:1 | 880 | 148 |
| 8 | 22 | .11 | .009 | .80:1 | 1600 | 230 |
| 9 | 50 | .253 | .370 | 1.46:1 | 1700 | 220 |

Note:
(1) 2,4,6-Trichlorophenol.

I claim:
1. The improved method of quantitatively determining the presence of chloromethyl methyl ether or bis-chloromethyl ether in a fluid which comprises:
   bringing a sample of said fluid into intimate admixture, in lower alcohol medium, with an alkali metal salt of a lower alcohol and with a readily detectable organic hydroxy compound selected from
   1. a compound of the formula R-OH wherein R is a halo-lower alkyl, a halophenyl, unsubstituted phenyl, an alkoxy halophenyl, an alkoxy phenyl, an alkyl halophenyl, an alkylphenyl or
   2. a halothiophenol or thiophenol or
   3. a halopyridinol or unsubstituted pyridinol, the molar ratio of said salt to said hydroxy compound being in the range of from about 0.2:1 to about 5:1, the total moles of said salt present in said lower alcohol medium being at least equal to the sum of the moles of chloromethyl methyl ether plus two times the moles of bis-chloromethyl ether present, and the total moles of said hydroxy compound present in said lower alcohol medium being at least equal to the sum of the moles of chloromethyl methyl ether and bis-chloromethyl ether present;
   adding to the admixture, (1) an aqueous medium selected from the group consisting of (a) water and (b) an aqueous solution of a salt former, and (2) an immiscible organic solvent;
   agitating the admixture and allowing the phases to separate;

drawing off at least a portion of the solvent phase containing ether derivative;

directing said solvent portion onto a suitable gas chromatographic column;

eluting with inert gas the solvent portion from the column and into an electron capture detector capable of detecting the said ether derivative;

and displaying the output of said detector on a read-out device.

2. The method as in claim 1 wherein the molar ratio of said salt to said hydroxy compound is about 1:1.

3. The method as in claim 1 wherein the admixture of sample, lower alcohol medium, alkali metal salt of lower alcohol and readily detectable organic hydroxy compound is warmed to a temperature of about 25° to about 100° C before adding said aqueous medium.

4. The method as in claim 1 wherein the molar concentration of each of said salt and said organic hydroxy compound is within the range of from about 0.03 to about 0.5 moles per liter of the alcohol.

5. The method as in claim 1 wherein the aqueous medium is employed in an amount within the range of from about 0.5 to 1.5 times the volume of the lower alcohol, and the organic solvent is employed in an amount within the range of from about 5 to about 25 percent of the volume of the lower alcohol.

6. The method as in claim 1 wherein the aqueous medium is an aqueous solution containing from about 1 to about 5 moles per liter of a salt former.

7. The method as in claim 1 wherein the lower alcohol is methanol, ethanol, n-propanol or isopropanol and the alkali metal salt is of the same alcohol as the lower alcohol present.

8. The method as in claim 1 wherein the molar concentration of each of said salt and said organic hydroxy compound is within the range of from about 0.03 to about 0.5 moles per liter of the alcohol; wherein the aqueous medium is employed in an amount within the range from about 0.5 to about 1.5 times the volume of the lower alcohol; wherein the organic solvent is employed in an amount within the range of from about 5 to about 25 percent of the volume of the lower alcohol; and with the proviso that where the molar ratio of said salt to said hydroxy compound is less than about 1:1, said aqueous medium is an aqueous solution containing from about 1 to about 5 moles per liter of a salt former.

9. The method as in claim 8 wherein the molar ratio of salt to hydroxy compound is about 1:1.

10. The method as in claim 8 wherein the admixture of sample, lower alcohol medium, alkali metal salt of lower alcohol and readily detectable organic hydroxy compound is warmed to a temperature of about 25° to about 100° C before adding said aqueous medium.

11. The method as in claim 8 wherein the lower alcohol is methanol, ethanol, n-propanol or isopropanol and the alkali metal salt is of the same alcohol as the lower alcohol present.

12. The method as in claim 8 wherein the readily detectable organic hydroxy compound is a halophenolic hydroxy compound.

13. The method as in claim 12 wherein the molar ratio of salt to hydroxy compound is about 1:1.

14. The method as in claim 12 wherein the admixture of sample, lower alcohol medium, alkali metal salt of lower alcohol and halophenolic hydroxy compound is warmed to a temperature of about 25 to about 100° C before adding said aqueous medium.

15. The method as in claim 12 wherein the lower alcohol is methanol, ethanol, n-propanol or isopropanol and the alkali metal salt is of the same alcohol as the lower alcohol present.

16. The method as in claim 12 wherein the readily detectable organic hydroxy compound is a chlorophenolic hydroxy compound or a bromophenolic hydroxy compound.

17. The method as in claim 12 wherein the readily detectable organic hydroxy compound is a perchlorophenolic hydroxy compound or a perbromophenolic hydroxy compound.

18. The method as in claim 12 wherein the readily detectable organic hydroxy compound is 2,4,6-trichlorophenol.

19. The method as in claim 12 wherein the lower alcohol is methanol, the said salt is sodium methoxide, and the halophenolic compound is 2,4,6-trichlorophenol.

20. The method as in claim 12 wherein the molar concentration of each of the halophenolic hydroxy compound and the salt in the lower alcohol is approximately 0.1 molar.

21. The method as in claim 12 wherein the immiscible organic solvent is selected from hexane, octane, isooctane, decane, pentane, benzene, alkyl benzene, and a mixture thereof.

22. The method as in claim 12 wherein the chromatographic column employed is packed with glass beads having a stationary liquid phase thereon.

23. The method as in claim 22 wherein the stationary liquid phase is a highly polar cyano silicone polymer.

24. The method as in claim 12 wherein the volume of immiscible organic solvent employed to extract the ether derivative is about 10 to about 20 percent of the volume of the lower alcohol employed.

25. The method as in claim 12 wherein the fluid is air.

26. The method as in claim 12 wherein the fluid is a liquid.

* * * * *

UNITED STATES PATENT AND TRADEMARK OFFICE
CERTIFICATE OF CORRECTION

PATENT NO. : 4,042,326                        Page 1 of 2

DATED : August 16, 1977

INVENTOR(S) : George J. Kallos

It is certified that error appears in the above-identified patent and that said Letters Patent are hereby corrected as shown below:

On the cover page, under "Other Publications", change "Ton et al" to --Tou et al--.

Col. 9, line 15, change "Anspic" to --Anspec--.

In the Table, delete the "2,4,6" over Col. 2 and move the heading "2,4,6-trichlorophenol" to the left so that it centers over Columns 2 and 3.

Col. 3, Run No. 8, change ".11" to --.111--.

UNITED STATES PATENT AND TRADEMARK OFFICE
CERTIFICATE OF CORRECTION

PATENT NO. : 4,042,326             Page 2 of 2
DATED        : August 16, 1977
INVENTOR(S) : George J. Kallos It is certified that error appears in the above–identified patent and that said Letters Patent are hereby corrected as shown below:

Insert a column after Col. 3 headed --gms/l--.

```
   25
    2.1
    3.5
   2
    4.4
    4.3
    7.7
   16
    4.8
   20
```

Also, move the heading over Col. 4, "NaOCH$_3$" to the left so that it centers over this new Col. 4 and Col. 5 "moles/l".

After the Column headed "NaOCH$_3$:TCP" insert --$^{(1)}$--.

In the heading over the last column of the Table, change "bis-CMe" to --bis-CME--.

Signed and Sealed this

Twenty-second Day of November 1977

[SEAL]

Attest:

RUTH C. MASON           LUTRELLE F. PARKER
*Attesting Officer*       *Acting Commissioner of Patents and Trademarks*